(12) United States Patent
Bowman et al.

(10) Patent No.: US 12,114,863 B2
(45) Date of Patent: Oct. 15, 2024

(54) IMPLANT DELIVERY SYSTEM (71) Applicant: MicroVention, Inc., Aliso Viejo, CA (US)

(72) Inventors: Heath Bowman, Trabuco Canyon, CA (US); Nga Ting Wong, Alhambra, CA (US); Diana N. Valencia, Hawaiian Gardens, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 364 days.

(21) Appl. No.: 16/705,097

(22) Filed: Dec. 5, 2019

(65) Prior Publication Data
US 2020/0178975 A1 Jun. 11, 2020

Related U.S. Application Data

(60) Provisional application No. 62/775,816, filed on Dec. 5, 2018.

(51) Int. Cl.
*A61B 17/12* (2006.01)
*A61B 17/00* (2006.01)
(Continued)

(52) U.S. Cl.
CPC .... *A61B 17/1214* (2013.01); *A61B 17/12113* (2013.01); *A61F 6/22* (2013.01);
(Continued)

(58) Field of Classification Search
CPC .. A61B 2017/12068; A61B 2090/3983; A61B 2017/12077; A61B 2017/1205; A61B 2017/12054; A61B 17/1214–12154
See application file for complete search history.

(56) References Cited

U.S. PATENT DOCUMENTS 3,324,280 A 6/1967 Cheney et al.
4,346,712 A 8/1982 Handa et al.
(Continued)

FOREIGN PATENT DOCUMENTS

CA 2493016 A1 2/2004
EP 1 538 997 B1 6/2005
(Continued)

OTHER PUBLICATIONS

Graves, V.B. et al., "Endovascular Occlusion of the Carotid or Vertebral Artery with Temporary Proximal Flow Arrest and Microcoils: Clinical Results," *AJNR Am J Neuroradiol* 18:1201-1206, American Society of Neuroradiology, Aug. 1997, 6 pages.
(Continued)

*Primary Examiner* — Sarah A Long
*Assistant Examiner* — Raihan R Khandker
(74) *Attorney, Agent, or Firm* — Inskeep IP Group, Inc.

(57) ABSTRACT

An implant delivery system having an implant-pusher junction that has improved flexibility due to a shortened heater and tapered marker band. The heater capsule includes a coil having a complex shape made possible through additive manufacturing. The complex shape generates increased heat over a shorter length when compared to traditional linear coils. The marker band includes a tapered end that allows the implant to pivot relative to the pusher.

21 Claims, 3 Drawing Sheets

(51) Int. Cl.
*A61B 90/00* (2016.01)
*A61F 6/22* (2006.01)
*A61F 2/01* (2006.01)
*A61F 2/966* (2013.01)

(52) U.S. Cl.
CPC ............ *A61B 2017/00526* (2013.01); *A61B 2017/00632* (2013.01); *A61B 2017/12068* (2013.01); *A61B 2090/3983* (2016.02); *A61F 2/011* (2020.05); *A61F 2002/9665* (2013.01)

(56) References Cited

U.S. PATENT DOCUMENTS

| | | | |
|---|---|---|---|
| 4,364,392 A | 12/1982 | Strother et al. | |
| 4,402,319 A | 9/1983 | Handa et al. | |
| 4,487,754 A | 12/1984 | Reed | |
| 4,512,338 A | 4/1985 | Balko et al. | |
| 4,545,367 A | 10/1985 | Tucci | |
| 4,551,132 A | 11/1985 | Pasztor et al. | |
| 4,638,803 A | 1/1987 | Rand | |
| RE32,348 E | 2/1987 | Pevsner | |
| 4,735,201 A | 4/1988 | O'Reilly | |
| 4,795,741 A | 1/1989 | Leshchiner et al. | |
| 4,819,637 A | 4/1989 | Dormandy, Jr. et al. | |
| 4,885,217 A | 12/1989 | Hoge | |
| 4,944,746 A | 7/1990 | Iwata et al. | |
| 4,994,069 A | 2/1991 | Ritchart et al. | |
| 5,001,009 A | 3/1991 | Whitbourne | |
| 5,059,213 A | 10/1991 | Chesterfield et al. | |
| 5,108,407 A | 4/1992 | Geremia et al. | |
| 5,122,136 A | 6/1992 | Guglielmi et al. | |
| 5,133,731 A | 7/1992 | Butler et al. | |
| 5,147,317 A | 9/1992 | Shank et al. | |
| 5,147,370 A | 9/1992 | McNamara et al. | |
| 5,163,952 A | 11/1992 | Froix | |
| 5,167,624 A | 12/1992 | Butler et al. | |
| 5,176,140 A | 1/1993 | Kami et al. | |
| 5,217,484 A | 6/1993 | Marks | |
| 5,226,911 A | 7/1993 | Chee et al. | |
| 5,242,452 A | 9/1993 | Inoue | |
| 5,250,071 A | 10/1993 | Palermo | |
| 5,256,146 A | 10/1993 | Ensminger et al. | |
| 5,258,042 A | 11/1993 | Mehta | |
| 5,261,916 A | 11/1993 | Engelson | |
| 5,269,030 A | 12/1993 | Pahno et al. | |
| 5,290,305 A | 3/1994 | Inoue | |
| 5,304,194 A | 4/1994 | Chee et al. | |
| 5,311,027 A | 5/1994 | Schuetz | |
| 5,312,415 A | 5/1994 | Palermo | |
| 5,331,027 A | 7/1994 | Whitbourne | |
| 5,334,201 A | 8/1994 | Cowan | |
| 5,334,210 A | 8/1994 | Gianturco | |
| 5,350,397 A | 9/1994 | Palermo et al. | |
| 5,354,295 A | 10/1994 | Guglielmi et al. | |
| 5,382,259 A | 1/1995 | Phelps et al. | |
| 5,382,260 A | 1/1995 | Dormandy, Jr. et al. | |
| 5,383,853 A | 1/1995 | Jung et al. | |
| 5,383,887 A | 1/1995 | Nadal | |
| 5,423,777 A | 6/1995 | Tajiri et al. | |
| 5,423,829 A | 6/1995 | Pham et al. | |
| 5,423,849 A | 6/1995 | Engelson et al. | |
| 5,433,708 A | 7/1995 | Nichols et al. | |
| 5,443,454 A | 8/1995 | Tanabe et al. | |
| 5,443,478 A | 8/1995 | Purdy | |
| 5,443,495 A | 8/1995 | Buscemi et al. | |
| 5,469,867 A | 11/1995 | Schmitt | |
| 5,470,338 A | 11/1995 | Whitfield et al. | |
| 5,476,472 A | 12/1995 | Dormandy | |
| 5,498,227 A | 3/1996 | Mawad | |
| 5,498,250 A | 3/1996 | Prather | |
| 5,522,836 A | 6/1996 | Palermo | |
| 5,525,334 A | 6/1996 | Ito et al. | |
| 5,529,653 A | 6/1996 | Glastra | |
| 5,536,274 A | 7/1996 | Neuss | |
| 5,540,680 A | 7/1996 | Guglielmi et al. | |
| 5,569,245 A | 10/1996 | Guglielmi et al. | |
| 5,578,074 A | 11/1996 | Mirigian | |
| 5,580,568 A | 12/1996 | Greff et al. | |
| 5,582,619 A | 12/1996 | Ken | |
| 5,593,412 A | 1/1997 | Martinez et al. | |
| 5,601,600 A | 2/1997 | Ton | |
| 5,609,608 A | 3/1997 | Benett et al. | |
| 5,612,050 A | 3/1997 | Rowe et al. | |
| 5,614,204 A | 3/1997 | Cochrum | |
| 5,624,449 A | 4/1997 | Pham et al. | |
| 5,624,461 A | 4/1997 | Mariant | |
| 5,624,685 A | 4/1997 | Takahashi et al. | |
| 5,634,936 A | 6/1997 | Linden et al. | |
| 5,639,277 A | 6/1997 | Mariant et al. | |
| 5,645,558 A | 7/1997 | Horton | |
| 5,658,308 A | 8/1997 | Snyder | |
| 5,667,767 A | 9/1997 | Greff et al. | |
| 5,669,905 A | 9/1997 | Scheldrup et al. | |
| 5,669,931 A | 9/1997 | Kupiecki et al. | |
| 5,676,671 A | 10/1997 | Inoue | |
| 5,690,667 A | 11/1997 | Gia | |
| 5,690,671 A | 11/1997 | McGurk et al. | |
| 5,700,258 A | 12/1997 | Mirigian et al. | |
| 5,702,361 A | 12/1997 | Evans et al. | |
| 5,718,711 A | 2/1998 | Berenstein et al. | |
| 5,722,989 A | 3/1998 | Fitch et al. | |
| 5,725,546 A | 3/1998 | Samson | |
| 5,725,568 A | 3/1998 | Hastings | |
| 5,733,329 A | 3/1998 | Wallace et al. | |
| 5,743,905 A | 4/1998 | Eder et al. | |
| 5,749,891 A | 5/1998 | Ken et al. | |
| 5,749,894 A | 5/1998 | Engelson | |
| 5,749,921 A | 5/1998 | Lenker et al. | |
| 5,750,585 A | 5/1998 | Park et al. | |
| 5,759,161 A | 6/1998 | Ogawa et al. | |
| 5,766,204 A | 6/1998 | Porter et al. | |
| 5,766,219 A | 6/1998 | Horton | |
| 5,792,154 A | 8/1998 | Doan et al. | |
| 5,800,454 A | 9/1998 | Jacobsen et al. | |
| 5,800,455 A | 9/1998 | Palermo et al. | |
| 5,814,062 A | 9/1998 | Sepetka et al. | |
| 5,823,198 A | 10/1998 | Jones et al. | |
| 5,830,178 A | 11/1998 | Jones et al. | |
| 5,830,230 A | 11/1998 | Berryman et al. | |
| 5,846,210 A | 12/1998 | Ogawa et al. | |
| 5,846,247 A | 12/1998 | Unsworth et al. | |
| 5,851,206 A | 12/1998 | Guglielmi et al. | |
| 5,851,508 A | 12/1998 | Greff et al. | |
| 5,853,418 A | 12/1998 | Ken et al. | |
| 5,855,578 A | 1/1999 | Guglielmi et al. | |
| 5,873,835 A | 2/1999 | Hastings et al. | |
| 5,879,499 A | 3/1999 | Corvi | |
| 5,891,058 A | 4/1999 | Taki et al. | |
| 5,891,130 A | 4/1999 | Palermo et al. | |
| 5,895,385 A | 4/1999 | Guglielmi et al. | |
| 5,902,254 A | 5/1999 | Magram | |
| 5,911,737 A | 6/1999 | Lee et al. | |
| 5,925,037 A | 7/1999 | Guglielmi et al. | |
| 5,925,059 A | 7/1999 | Palermo et al. | |
| 5,925,061 A | 7/1999 | Ogi et al. | |
| 5,928,226 A | 7/1999 | Guglielmi et al. | |
| 5,941,888 A | 8/1999 | Wallace et al. | |
| 5,944,714 A | 8/1999 | Guglielmi et al. | |
| 5,944,733 A | 8/1999 | Engelson | |
| 5,947,962 A | 9/1999 | Guglielmi et al. | |
| 5,947,963 A | 9/1999 | Guglielmi | |
| 5,964,771 A | 10/1999 | Beyar et al. | |
| 5,964,797 A | 10/1999 | Ho | |
| 5,976,126 A | 11/1999 | Guglielmi | |
| 5,976,131 A | 11/1999 | Guglielmi et al. | |
| 5,984,629 A | 11/1999 | Brodersen et al. | |
| 5,984,929 A | 11/1999 | Bashiri et al. | |
| 5,984,944 A * | 11/1999 | Forber | A61B 17/12022 606/191 |
| 5,989,242 A | 11/1999 | Saadat et al. | |
| 6,010,498 A | 1/2000 | Guglielmi | |
| 6,013,084 A | 1/2000 | Ken et al. | |
| 6,015,424 A | 1/2000 | Rosenbluth et al. | |
| 6,033,423 A | 3/2000 | Ken et al. | |

(56) References Cited

U.S. PATENT DOCUMENTS

| | | |
|---|---|---|
| 6,048,338 A | 4/2000 | Larson et al. |
| 6,053,873 A | 4/2000 | Govari et al. |
| 6,056,759 A | 5/2000 | Fiedler |
| 6,059,815 A | 5/2000 | Lee et al. |
| 6,063,070 A | 5/2000 | Eder |
| 6,063,100 A | 5/2000 | Diaz et al. |
| 6,066,133 A | 5/2000 | Guglielmi et al. |
| 6,068,644 A | 5/2000 | Lulo et al. |
| 6,077,291 A | 6/2000 | Das |
| 6,083,220 A | 7/2000 | Guglielmi et al. |
| 6,086,599 A | 7/2000 | Lee et al. |
| 6,091,980 A | 7/2000 | Squire et al. |
| 6,102,932 A | 8/2000 | Kurz |
| 6,102,933 A | 8/2000 | Lee et al. |
| 6,117,142 A | 9/2000 | Goodson et al. |
| 6,159,206 A | 12/2000 | Ogawa |
| 6,165,178 A | 12/2000 | Bashiri et al. |
| 6,183,491 B1 | 2/2001 | Lulo |
| 6,183,504 B1 | 2/2001 | Inoue |
| 6,193,728 B1 | 2/2001 | Ken et al. |
| 6,221,066 B1 | 4/2001 | Ferrera et al. |
| 6,224,609 B1 | 5/2001 | Ressemann et al. |
| 6,224,610 B1 | 5/2001 | Ferrera |
| 6,238,403 B1 | 5/2001 | Greene, Jr. et al. |
| 6,238,415 B1 | 5/2001 | Sepetka et al. |
| 6,270,520 B1 | 8/2001 | Inoue |
| 6,277,126 B1 | 8/2001 | Barry et al. |
| 6,287,318 B1 | 9/2001 | Villar et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,312,407 B1 | 11/2001 | Zadno-Azizi et al. |
| 6,319,267 B1 | 11/2001 | Kurz |
| 6,338,657 B1 | 1/2002 | Harper et al. |
| 6,361,547 B1 | 3/2002 | Hieshima |
| 6,371,979 B1 | 4/2002 | Beyar et al. |
| 6,375,668 B1 | 4/2002 | Gifford et al. |
| 6,375,669 B1 | 4/2002 | Rosenbluth et al. |
| 6,383,204 B1 | 5/2002 | Ferrera et al. |
| 6,397,850 B1 | 6/2002 | Scheldrup et al. |
| 6,425,893 B1 | 7/2002 | Guglielmi |
| 6,428,557 B1 | 8/2002 | Hilaire |
| 6,440,098 B1 | 8/2002 | Luscher |
| 6,447,522 B2 | 9/2002 | Gambale et al. |
| 6,454,780 B1 | 9/2002 | Wallace |
| 6,478,773 B1 | 11/2002 | Ghandi et al. |
| 6,494,884 B2 | 12/2002 | Gifford, III et al. |
| 6,500,149 B2 | 12/2002 | Gandhi et al. |
| 6,514,264 B1 | 2/2003 | Naglreiter |
| 6,514,282 B1 | 2/2003 | Inoue |
| 6,526,979 B1 | 3/2003 | Nikolchev et al. |
| 6,537,284 B1 | 3/2003 | Inoue |
| 6,544,225 B1 | 4/2003 | Lulo et al. |
| 6,551,305 B2 | 4/2003 | Ferrera et al. |
| 6,551,340 B1 | 4/2003 | Konya et al. |
| 6,554,849 B1 | 4/2003 | Jones et al. |
| 6,585,718 B2 | 7/2003 | Hayzelden et al. |
| 6,602,261 B2 | 8/2003 | Greene, Jr. et al. |
| 6,602,269 B2 | 8/2003 | Wallace et al. |
| 6,607,538 B1 | 8/2003 | Ferrera et al. |
| 6,610,046 B1 | 8/2003 | Usami et al. |
| 6,634,361 B1 | 10/2003 | Nikolchev et al. |
| 6,645,240 B2 | 11/2003 | Yee |
| 6,656,173 B1 | 12/2003 | Palermo |
| 6,684,884 B2 | 2/2004 | Nikolchev et al. |
| 6,689,141 B2 | 2/2004 | Ferrera et al. |
| 6,705,323 B1 | 3/2004 | Nikolchev et al. |
| 6,716,238 B2 | 4/2004 | Elliott |
| 6,740,073 B1 | 5/2004 | Saville |
| 6,743,236 B2 | 6/2004 | Barry et al. |
| 6,743,251 B1 | 6/2004 | Eder |
| 6,807,446 B2 | 10/2004 | Fenn et al. |
| 6,849,081 B2 | 2/2005 | Sepetka et al. |
| 6,849,087 B1 | 2/2005 | Chuter |
| 6,855,125 B2 | 2/2005 | Shanley |
| 6,895,276 B2 | 5/2005 | Kast et al. |
| 6,905,503 B2 | 6/2005 | Gifford, III et al. |
| 6,953,465 B2 | 10/2005 | Dieck et al. |
| 6,953,473 B2 | 10/2005 | Porter |
| 6,958,068 B2 | 10/2005 | Hieshima |
| 6,964,671 B2 | 11/2005 | Cheng et al. |
| 6,966,892 B2 | 11/2005 | Ghandi et al. |
| 6,989,020 B2 | 1/2006 | Jones et al. |
| 7,001,422 B2 | 2/2006 | Escamilla et al. |
| 7,014,645 B2 | 3/2006 | Greene, Jr. et al. |
| 7,048,719 B1 | 5/2006 | Monetti |
| 7,063,671 B2 | 6/2006 | Couvillon, Jr. |
| 7,063,707 B2 | 6/2006 | Bose et al. |
| 7,066,904 B2 | 6/2006 | Rosenthal et al. |
| 7,070,609 B2 | 7/2006 | West |
| 7,108,708 B2 | 9/2006 | Cheng et al. |
| 7,137,990 B2 | 11/2006 | Herbert et al. |
| 7,147,618 B2 | 12/2006 | Kurz |
| 7,166,122 B2 | 1/2007 | Aganon et al. |
| 7,179,276 B2 | 2/2007 | Barry et al. |
| 7,182,774 B2 | 2/2007 | Barry et al. |
| 7,198,613 B2 | 4/2007 | Gandhi et al. |
| 7,201,768 B2 | 4/2007 | Diaz et al. |
| 7,208,003 B2 | 4/2007 | Davis et al. |
| 7,238,194 B2 | 7/2007 | Monstdt et al. |
| 7,255,707 B2 | 8/2007 | Ramzipoor et al. |
| 7,264,628 B2 | 9/2007 | Jones et al. |
| 7,270,674 B2 | 9/2007 | Jones et al. |
| 7,309,345 B2 | 12/2007 | Wallace |
| 7,323,000 B2 | 1/2008 | Monstdt et al. |
| 7,326,225 B2 | 2/2008 | Ferrera et al. |
| 7,344,558 B2 | 3/2008 | Lorenzo et al. |
| 7,351,254 B2 | 4/2008 | Magers |
| 7,357,809 B2 | 4/2008 | Jones et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,513,878 B2 | 4/2009 | Hamilton |
| 7,553,321 B2 | 6/2009 | Litzenberg et al. |
| 7,575,582 B2 | 8/2009 | Gandhi et al. |
| 7,578,826 B2 | 8/2009 | Gandhi et al. |
| 7,582,101 B2 | 9/2009 | Jones et al. |
| 7,585,317 B2 | 9/2009 | Davidson et al. |
| 7,591,833 B2 | 9/2009 | Jones et al. |
| 7,608,089 B2 | 10/2009 | Wallace et al. |
| RE41,029 E | 12/2009 | Guglielmi et al. |
| 7,628,797 B2 | 12/2009 | Tieu et al. |
| 7,651,513 B2 | 1/2010 | Teoh et al. |
| 7,691,118 B2 | 4/2010 | Gorospe |
| 7,691,121 B2 | 4/2010 | Rosenbluth et al. |
| 7,691,124 B2 | 4/2010 | Balgobin |
| 7,708,754 B2 | 5/2010 | Balgobin et al. |
| 7,708,755 B2 | 5/2010 | Davis, III et al. |
| 7,740,637 B2 | 6/2010 | Gandhi et al. |
| 7,771,451 B2 | 8/2010 | Ramzipoor |
| 7,776,054 B2 | 8/2010 | Gandhi et al. |
| 7,780,645 B2 | 8/2010 | Jones |
| 7,780,680 B2 | 8/2010 | Gandhi et al. |
| 7,789,891 B2 | 9/2010 | Wallace |
| 7,811,305 B2 | 10/2010 | Balgobin et al. |
| 7,918,872 B2 | 4/2011 | Mitelberg et al. |
| 7,924,636 B2 | 4/2011 | Morimoto et al. |
| 7,942,894 B2 | 5/2011 | West |
| 7,947,060 B2 | 5/2011 | Mazzocchi et al. |
| RE42,662 E | 8/2011 | Guglielmi et al. |
| RE42,756 E | 9/2011 | Guglielmi et al. |
| 8,034,073 B2 | 10/2011 | Davis, III et al. |
| 8,034,094 B2 | 10/2011 | Aoba et al. |
| 8,114,145 B2 | 2/2012 | Hartley et al. |
| 8,142,455 B2 | 3/2012 | Thompson et al. |
| 8,182,506 B2 | 5/2012 | Fitz et al. |
| 8,192,480 B2 | 6/2012 | Tieu et al. |
| 8,206,413 B2 | 6/2012 | Jones et al. |
| 8,267,955 B2 | 9/2012 | Patterson et al. |
| 8,460,332 B2 | 6/2013 | Tieu et al. |
| 8,652,163 B2 | 2/2014 | Padilla et al. |
| 8,728,142 B2 | 5/2014 | Gandhi et al. |
| 8,795,316 B2 | 8/2014 | Balgobin et al. |

(56) References Cited

U.S. PATENT DOCUMENTS

| | | |
|---|---|---|
| 8,864,790 B2 | 10/2014 | Strauss et al. |
| 8,932,317 B2 | 1/2015 | Marks et al. |
| 8,956,381 B2 | 2/2015 | Que et al. |
| 8,998,926 B2 | 4/2015 | Pomeranz |
| 9,242,070 B2 | 1/2016 | Tieu |
| 9,265,504 B2 | 2/2016 | Kellett |
| 9,301,862 B2 | 4/2016 | Jordan et al. |
| 9,307,996 B2 | 4/2016 | Johnson et al. |
| 9,414,819 B2 | 8/2016 | Fitz et al. |
| 9,486,223 B2 | 11/2016 | Que et al. |
| 9,504,475 B2 | 11/2016 | Chen et al. |
| 9,510,962 B2 | 12/2016 | Aoba et al. |
| 9,717,500 B2 | 8/2017 | Tieu et al. |
| 9,775,620 B2 | 10/2017 | Teoh et al. |
| 9,788,840 B2 | 10/2017 | Marks et al. |
| 9,814,465 B2 | 11/2017 | Win et al. |
| 9,867,622 B2 | 1/2018 | Bowman |
| 9,889,028 B2 | 2/2018 | Rasmussen et al. |
| 10,299,755 B2 | 5/2019 | Tieu |
| 10,413,302 B2 | 9/2019 | Fitz et al. |
| 10,478,192 B2 | 11/2019 | Teoh et al. |
| 10,524,799 B2 | 1/2020 | O'Connor et al. |
| 10,813,779 B2 | 10/2020 | Fleming, III et al. |
| 10,932,926 B2 | 3/2021 | Bar et al. |
| 2001/0029352 A1 | 10/2001 | Gandhi et al. |
| 2001/0041898 A1 | 11/2001 | Barry et al. |
| 2001/0044633 A1 | 11/2001 | Klint |
| 2001/0049521 A1 | 12/2001 | Gia et al. |
| 2002/0029035 A1 | 3/2002 | Lee et al. |
| 2002/0046756 A1 | 4/2002 | Laizzo et al. |
| 2002/0091380 A1 | 7/2002 | Wheelock et al. |
| 2002/0099408 A1 | 7/2002 | Marks et al. |
| 2002/0107534 A1 | 8/2002 | Schaefer et al. |
| 2002/0123755 A1 | 9/2002 | Lowe et al. |
| 2002/0173837 A1 | 11/2002 | Lauterjung |
| 2002/0188341 A1 | 12/2002 | Elliott |
| 2003/0023262 A1 | 1/2003 | Welch |
| 2003/0045859 A1 | 3/2003 | Dominguez |
| 2003/0045901 A1 | 3/2003 | Opolski |
| 2003/0069539 A1 | 4/2003 | Gandhi et al. |
| 2003/0125790 A1 | 7/2003 | Fastovsky et al. |
| 2004/0002731 A1 | 1/2004 | Aganon et al. |
| 2004/0002733 A1 | 1/2004 | Teoh |
| 2004/0034363 A1 | 2/2004 | Wilson et al. |
| 2004/0044385 A1 | 3/2004 | Fenn et al. |
| 2004/0111029 A1 | 6/2004 | Bates et al. |
| 2004/0181177 A1 | 9/2004 | Lee et al. |
| 2004/0204701 A1 | 10/2004 | Cox et al. |
| 2004/0220563 A1 | 11/2004 | Eder |
| 2005/0021023 A1 | 1/2005 | Guglielmi et al. |
| 2005/0043755 A1 | 2/2005 | Wilson et al. |
| 2005/0113864 A1 | 5/2005 | Gandhi et al. |
| 2005/0118865 A1 | 6/2005 | Henningsen |
| 2005/0131523 A1 | 6/2005 | Bashiri et al. |
| 2005/0149108 A1 | 7/2005 | Cox |
| 2005/0154417 A1 | 7/2005 | Sepetka et al. |
| 2005/0154440 A1 | 7/2005 | Limon |
| 2005/0171572 A1 | 8/2005 | Martinez |
| 2005/0222580 A1 | 10/2005 | Gifford, III et al. |
| 2005/0273020 A1 | 12/2005 | Whittaker et al. |
| 2005/0283182 A1 | 12/2005 | Pierce et al. |
| 2006/0025801 A1 | 2/2006 | Lulo et al. |
| 2006/0025802 A1 | 2/2006 | Sowers |
| 2006/0025803 A1 | 2/2006 | Mitelberg et al. |
| 2006/0036280 A1 | 2/2006 | French et al. |
| 2006/0052815 A1 | 3/2006 | Fitz et al. |
| 2006/0079923 A1 | 4/2006 | Chhabra et al. |
| 2006/0116584 A1 | 6/2006 | Sudol et al. |
| 2006/0116708 A1 | 6/2006 | Ogawa et al. |
| 2006/0116714 A1 | 6/2006 | Sepetka et al. |
| 2006/0135986 A1 | 6/2006 | Wallace et al. |
| 2006/0173488 A1 | 8/2006 | Takeuchi et al. |
| 2006/0184092 A1 | 8/2006 | Atanasoska et al. |
| 2006/0200192 A1 | 9/2006 | Fitz et al. |
| 2006/0241682 A1 | 10/2006 | Kurz |
| 2006/0241684 A1 | 10/2006 | Wilson et al. |
| 2006/0241685 A1 | 10/2006 | Wilson et al. |
| 2006/0253023 A1 | 11/2006 | Lewis et al. |
| 2006/0253149 A1 | 11/2006 | Gandhi et al. |
| 2006/0271097 A1 | 11/2006 | Ramzipoor et al. |
| 2006/0271098 A1 | 11/2006 | Peacock, III |
| 2006/0271099 A1 | 11/2006 | Marks et al. |
| 2006/0276825 A1 | 12/2006 | Mitelberg et al. |
| 2006/0276826 A1 | 12/2006 | Mitelberg et al. |
| 2006/0276829 A1 | 12/2006 | Balgobin et al. |
| 2006/0276830 A1 | 12/2006 | Balgobin et al. |
| 2006/0276834 A1 | 12/2006 | Balgobin et al. |
| 2007/0010849 A1 | 1/2007 | Balgobin et al. |
| 2007/0055302 A1 | 3/2007 | Henry et al. |
| 2007/0073334 A1 | 3/2007 | Ramzipoor |
| 2007/0100419 A1 | 5/2007 | Licata et al. |
| 2007/0104752 A1 | 5/2007 | Lee et al. |
| 2007/0123927 A1 | 5/2007 | Farnan |
| 2007/0123928 A1* | 5/2007 | Farnan ............... A61B 17/1214 606/200 |
| 2007/0167911 A1 | 7/2007 | Gandhi et al. |
| 2007/0185443 A1 | 8/2007 | Euteneuer et al. |
| 2007/0185457 A1 | 8/2007 | Euteneuer et al. |
| 2007/0191879 A1 | 8/2007 | Gandhi et al. |
| 2007/0203452 A1 | 8/2007 | Mehta |
| 2007/0208276 A1 | 9/2007 | Kornkven Volk et al. |
| 2007/0221230 A1 | 9/2007 | Thompson et al. |
| 2007/0239141 A1 | 10/2007 | Hartley et al. |
| 2007/0239193 A1 | 10/2007 | Simon et al. |
| 2007/0239196 A1 | 10/2007 | Pomeranz |
| 2007/0249924 A1 | 10/2007 | Takata et al. |
| 2007/0265637 A1 | 11/2007 | Andreas et al. |
| 2007/0270903 A1 | 11/2007 | Davis, III et al. |
| 2007/0299461 A1* | 12/2007 | Elliott ............... A61B 17/1214 606/191 |
| 2008/0045997 A1 | 2/2008 | Balgobin et al. |
| 2008/0097462 A1 | 4/2008 | Mitelberg et al. |
| 2008/0103585 A1 | 5/2008 | Monstadt et al. |
| 2008/0119887 A1 | 5/2008 | Que et al. |
| 2008/0119891 A1 | 5/2008 | Miles et al. |
| 2008/0125855 A1 | 5/2008 | Henkes et al. |
| 2008/0133028 A1 | 6/2008 | Wilson et al. |
| 2008/0140111 A1 | 6/2008 | Wilson et al. |
| 2008/0140178 A1 | 6/2008 | Rasmussen et al. |
| 2008/0147201 A1 | 6/2008 | Wilson et al. |
| 2008/0172119 A1 | 7/2008 | Yamasaki et al. |
| 2008/0221554 A1 | 9/2008 | O'Connor et al. |
| 2008/0221654 A1 | 9/2008 | Buiser et al. |
| 2008/0228215 A1 | 9/2008 | Strauss et al. |
| 2008/0243218 A1 | 10/2008 | Bottomley et al. |
| 2008/0246231 A1 | 10/2008 | Sjostedt et al. |
| 2008/0275464 A1 | 11/2008 | Abrams et al. |
| 2008/0283066 A1 | 11/2008 | Delgado et al. |
| 2008/0287982 A1 | 11/2008 | Harreld |
| 2008/0306503 A1 | 12/2008 | Que et al. |
| 2009/0018653 A1 | 1/2009 | Bashiri et al. |
| 2009/0024154 A1 | 1/2009 | Williams et al. |
| 2009/0054905 A1 | 2/2009 | Levy |
| 2009/0062726 A1 | 3/2009 | Ford et al. |
| 2009/0062812 A1 | 3/2009 | Fitz et al. |
| 2009/0076540 A1 | 3/2009 | Marks et al. |
| 2009/0082842 A1 | 3/2009 | Glynn |
| 2009/0099592 A1 | 4/2009 | Buiser et al. |
| 2009/0138036 A1 | 5/2009 | Nardone et al. |
| 2009/0143786 A1 | 6/2009 | Bashiri et al. |
| 2009/0163780 A1 | 6/2009 | Tieu |
| 2009/0163986 A1 | 6/2009 | Tieu et al. |
| 2009/0177261 A1 | 7/2009 | Teoh et al. |
| 2009/0254111 A1 | 10/2009 | Monstadt et al. |
| 2009/0270901 A1 | 10/2009 | Kelleher et al. |
| 2009/0270903 A1 | 10/2009 | Litzenberg et al. |
| 2009/0275971 A1 | 11/2009 | Kelleher et al. |
| 2009/0299275 A1 | 12/2009 | Gandhi et al. |
| 2009/0318892 A1 | 12/2009 | Aboytes et al. |
| 2010/0004731 A1 | 1/2010 | Gandhi et al. |
| 2010/0042133 A1 | 2/2010 | Ramzipoor et al. |
| 2010/0069838 A1 | 3/2010 | Weber et al. |
| 2010/0094395 A1 | 4/2010 | Kellett |
| 2010/0106162 A1 | 4/2010 | Jaeger et al. |

(56) References Cited

U.S. PATENT DOCUMENTS

| | | | |
|---|---|---|---|
| 2010/0152650 A1 | 6/2010 | Schrodt | |
| 2010/0152828 A1 | 6/2010 | Pakbaz et al. | |
| 2010/0160944 A1* | 6/2010 | Teoh | A61B 17/12154 606/191 |
| 2010/0160953 A1 | 6/2010 | Ngo et al. | |
| 2010/0160983 A1 | 6/2010 | Runco et al. | |
| 2010/0199448 A1 | 8/2010 | Vazales et al. | |
| 2010/0234872 A1 | 9/2010 | Guo et al. | |
| 2010/0249823 A1 | 9/2010 | Gandhi et al. | |
| 2010/0256666 A1 | 10/2010 | Chen et al. | |
| 2010/0268158 A1 | 10/2010 | Porter | |
| 2010/0268201 A1 | 10/2010 | Tieu et al. | |
| 2010/0268204 A1 | 10/2010 | Tieu et al. | |
| 2010/0268251 A1 | 10/2010 | Chen et al. | |
| 2010/0268252 A1 | 10/2010 | Chen et al. | |
| 2011/0046282 A1 | 2/2011 | Mizuta et al. | |
| 2011/0059639 A1 | 3/2011 | Dilmaghanian et al. | |
| 2011/0092997 A1 | 4/2011 | Kang | |
| 2011/0106098 A1 | 5/2011 | Williams | |
| 2011/0160824 A1 | 6/2011 | Ware et al. | |
| 2011/0301686 A1 | 12/2011 | Bowman et al. | |
| 2011/0313443 A1* | 12/2011 | Lorenzo | A61B 17/12022 606/200 |
| 2012/0041470 A1* | 2/2012 | Shrivastava | A61B 17/12031 606/200 |
| 2012/0065667 A1 | 3/2012 | Javois et al. | |
| 2012/0116350 A1 | 5/2012 | Strauss et al. | |
| 2012/0315798 A1 | 12/2012 | Poon et al. | |
| 2013/0012046 A1 | 1/2013 | Jullien et al. | |
| 2013/0085520 A1 | 4/2013 | Liang et al. | |
| 2013/0138136 A1* | 5/2013 | Beckham | A61B 17/12136 29/520 |
| 2013/0245745 A1 | 9/2013 | Vong et al. | |
| 2013/0261656 A1 | 10/2013 | Lorenzo | |
| 2013/0261657 A1 | 10/2013 | Lorenzo | |
| 2014/0058434 A1 | 2/2014 | Jones et al. | |
| 2014/0142611 A1 | 5/2014 | Plaza et al. | |
| 2014/0206958 A1 | 7/2014 | Laramy et al. | |
| 2014/0236127 A1* | 8/2014 | Lee | A61B 17/1214 606/191 |
| 2014/0277092 A1 | 9/2014 | Teoh et al. | |
| 2014/0277093 A1 | 9/2014 | Guo et al. | |
| 2014/0277094 A1 | 9/2014 | Chen et al. | |
| 2015/0057700 A1 | 2/2015 | Chen et al. | |
| 2015/0173772 A1 | 6/2015 | Bowman et al. | |
| 2015/0173773 A1* | 6/2015 | Bowman | A61M 25/0067 604/95.05 |
| 2015/0289879 A1* | 10/2015 | Bowman | A61B 17/12109 606/200 |
| 2016/0081693 A1 | 3/2016 | Lorenzo | |
| 2016/0345904 A1 | 12/2016 | Bowman | |
| 2017/0105739 A1* | 4/2017 | Dias | A61B 90/39 |
| 2018/0078263 A1* | 3/2018 | Stoppenhagen | A61B 17/12113 |
| 2018/0338767 A1 | 11/2018 | Dasnurkar et al. | |
| 2019/0192162 A1* | 6/2019 | Lorenzo | A61B 17/12109 |

FOREIGN PATENT DOCUMENTS

| | | |
|---|---|---|
| EP | 1 738 698 A2 | 1/2007 |
| EP | 1 884 208 A1 | 2/2008 |
| EP | 1 120 088 B1 | 4/2009 |
| EP | 1 886 632 B1 | 4/2011 |
| JP | S52141092 A | 11/1977 |
| JP | S5643962 A | 4/1981 |
| JP | H0247219 B2 | 12/1988 |
| JP | H01238874 A | 9/1989 |
| JP | 5158069 A | 6/1993 |
| JP | H0966109 A | 3/1997 |
| JP | H10127647 A | 5/1998 |
| WO | WO 1994/006503 A1 | 3/1994 |
| WO | WO 1995/027443 A1 | 10/1995 |
| WO | WO 1998/040033 A3 | 9/1998 |
| WO | WO 1999/006097 A1 | 2/1999 |
| WO | WO 2002/055146 A1 | 7/2002 |
| WO | WO 2004/008974 A1 | 1/2004 |
| WO | WO 2004/010877 A1 | 2/2004 |
| WO | WO 2006/126474 A1 | 11/2006 |
| WO | WO 2007/070788 A2 | 6/2007 |
| WO | WO 2007/070793 A2 | 6/2007 |
| WO | WO 2013/149684 A1 | 10/2013 |

OTHER PUBLICATIONS

Rosenthal M.D., D. et al., "Endovascular infrainguinal in situ saphenous vein bypass: A multicenter preliminary report," *J. Vasc Surg* Sep. 1992, vol. 3, No. 16, pp. 453-458, 6 pages.

Rosenthal, D. et al., "Angioscope-assisted endovascular occlusion of venous tributaries: preclinical studies," *Cardiovasc Surg* Jun. 1993, vol. 1, No. 3, pp. 225-227, 3 pages.

Schmutz, F. et al., "Embolization of Cerebral Arteriovenous Malformations with Silk: Histophathologic Changes and Hemorrhagic Complications," *AJNR Am J Neuroradiol* 18: 1233-1237, Aug. 1997, 5 pages.

Viñuela M.D., F. et al., "Guglielmi detachable coil embolization of acute intracranial aneurysm: perioperative anatomical and clinical outcome in 403 patients," *J Neurosurg* 86:475-486, Mar. 1997, 8 pages.

WIPO, European International Search Authority, International Search Report dated Nov. 27, 2000 in International Patent Application No. PCT/US2000/015445, 6 pages.

WIPO, U.S. International Search Authority, International Search Report mailed Mar. 19, 2009 in International Patent Application No. PCT/US2008/087855, 8 pages.

WIPO, U.S. International Search Authority, International Search Report mailed May 28, 2002 in International Patent Application No. PCT/US2001/032588, 5 pages.

WIPO, U.S. International Search Authority, International Search Report and Written Opinion mailed Jul. 9, 2015 in International Patent Application No. PCT/US2015/025594, 10 pages.

WIPO, U.S. International Search Authority, International Search Report and Written Opinion mailed May 27, 2014 in International Patent Application No. PCT/US2014/019155, 10pages.

WIPO, U.S. International Search Authority, International Search Report and Written Opinion mailed Jun. 8, 2010 in International Patent Application No. PCT/US2010/031268, 9 pages.

WIPO, U.S. International Search Authority, International Search Report and Written Opinion mailed Oct. 20, 2008 in International Patent Application No. PCT/US2008/071325, 10 pages.

\* cited by examiner

IMPLANT DELIVERY SYSTEM

RELATED APPLICATIONS

This application claims priority to U.S. Provisional Application Ser. No. 62/775,816 filed Dec. 5, 2018 entitled Implant Delivery System, which is hereby incorporated herein by reference in its entirety.

FIELD OF THE INVENTION

The present invention relates to systems and methods for delivering implant devices to a target site or location within the body of a patient.

BACKGROUND OF THE INVENTION

Delivery of implantable therapeutic devices by less invasive means has been demonstrated to be desirable in numerous clinical situations. For example, vascular embolization has been used to control vascular bleeding, to occlude the blood supply to tumors, to occlude fallopian tubes, and to occlude vascular aneurysms, particularly intracranial aneurysms. In recent years, vascular embolization for the treatment of aneurysms has received much attention. Implants used to treat aneurysms are often convoluted or coiled lengths of wound wire and are referred to as "microcoils." Microcoils work by filling an aneurysm causing the blood flow through the aneurysm to slow or stop, thereby inducing thrombosis within the aneurysm.

Vascular aneurysms can have extremely thin walls and puncturing an aneurysm wall results in a stroke. Because the walls are so delicate, microcoils are extremely flexible and have very little structural integrity. These microcoils are connected to a pusher system to enable delivery to the treatment site. Ideally, the microcoils and pusher would be sufficiently flexible in order to navigate the vasculature and enable placement within the aneurysm region. However, with traditional designs, there can be significant stiffness, particularly at the pusher-implant connection junction at the proximal end of the microcoil implant.

This rigidity of the proximal end of the coil can be partially attributed to the connection the coil has with the pusher, which is typically attached to the implant and is used to drive the pusher out of a delivery catheter. Often, the proximal end of the coil includes a rigid cylindrical marker band that is held against the distal end of the pusher, adding rigidity to the coil. Additionally, a heater element contained within the distal end of the pusher prevents bending of the distal tip of the pusher, resulting in a rigid implant-pusher junction that increases delivery difficulty. The combination of the heater coil and the marker band thus results in a rigid length at the junction of the implant and the device.

Though several coils and delivery systems have been developed, none have specifically addressed the rigidity at the junction of the implant and the pusher that is due to the sizes and shapes of the implant marker band and/or the length of the heater. Examples of these coils and detachment systems for implant devices are described in the prior art including U.S. Pat. No. 5,895,385 to Guglielmi et al. and U.S. Pat. No. 5,108,407 to Geremia et al., the contents of which are hereby incorporated by reference. Examples of systems using a heater to detach an implant device are disclosed in U.S. Pat. No. 9,867,622 to Bowman, U.S. Pat. No. 6,500,149 to Gandhi et al. and U.S. Pat. No. 4,346,712 to Handa et al., the contents of which are hereby incorporated by reference, describe the use of a heater to detach and deploy the implant device. Additionally, U.S. Pat. No. 8,182,506 to Fitz et al., U.S. Patent Pub. No. 2010/0268204 to Teiu et al., and U.S. Patent Pub. No. 2011/0301686 to Bowman et al., also pertain to thermal detachment systems and are hereby incorporated by reference in their entireties.

It would thus be desirable to develop a coil delivery system that maintains flexibility at the junction of the coil and the pusher. Such a device would promote ease of coil and device positioning during delivery as well as the prevention of coil migration out of the aneurysm after release.

SUMMARY OF THE INVENTION

The present invention pertains to a heater and a marker band designed for use with an implant delivery and detachment system used to position and deploy implantable devices such as coils, stents, filters, and the like within a body cavity including, but not limited to, blood vessels, fallopian tubes, malformations such as fistula and aneurysms, heart defects (e.g. left atrial appendages and sepal openings), and other luminal organs.

The heater designs of the present invention include complex shapes and a double-element design made possible through modern manufacturing techniques. The double-element design shortens the length of the heater necessary to achieve the temperatures needed for coil detachment. Heater elements are typically rigid. If a heater element were to flex, it is likely that adjacent windings would make contact with each other and create a short for the current to bypass the windings. Because heater elements are typically rigid, a shorter heater results in a more flexible pusher tip.

In at least one embodiment the heater is created via 3d printing techniques. Typical heaters utilize coils are formed by winding a single length of wire into a coil. The wire has a resistive quality that generates heat as current passes through the windings. Longer coils offer more resistance and thus generate more heat. As such, the coil must be sufficiently long in order to generate enough heat to sever or melt a connecting member (e.g. a tether) to detach the embolic coil. Using 3d printing techniques, vapor deposition, or additive layer concepts, it would be possible to create a multi-layered heating element that incorporates complex geometries to generate more heat for a given length than a traditional heater coil.

In at least one embodiment, the heater utilizes a plurality of connected planes each including an outer incomplete ring and an inner incomplete ring in the form of a C. The complex shape results in a much longer path for current to travel for a given overall heater length than a traditional coil of a similar length would provide. Thus, much more heat is generated. In some embodiments, a protective shell and dielectric material such as polyimide, parylene, and ceramic can be added to the heater to provide insulation between layers.

One aspect provides an implant delivery system that includes a pusher and a heater capsule at a distal end of the pusher. The heater capsule has an outer capsule and a heater element inside the outer capsule. The heater element defines a plurality of planes, each plane including an inner ring and an outer ring. One of the inner ring and the outer ring of each plane is connected to an inner ring or an outer ring, respectively, of an adjacent plane. The heater element also has an electrical connection to the outer capsule. A first lead wire connects the heater element to a power source and a second lead wire connects the outer capsule to the power source.

The marker band is shaped to allow the coil to pivot around the distal end of the pusher prior to release. This configuration significantly increases the flexibility of the interface between the coil and the delivery system.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF THE INVENTION

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1:
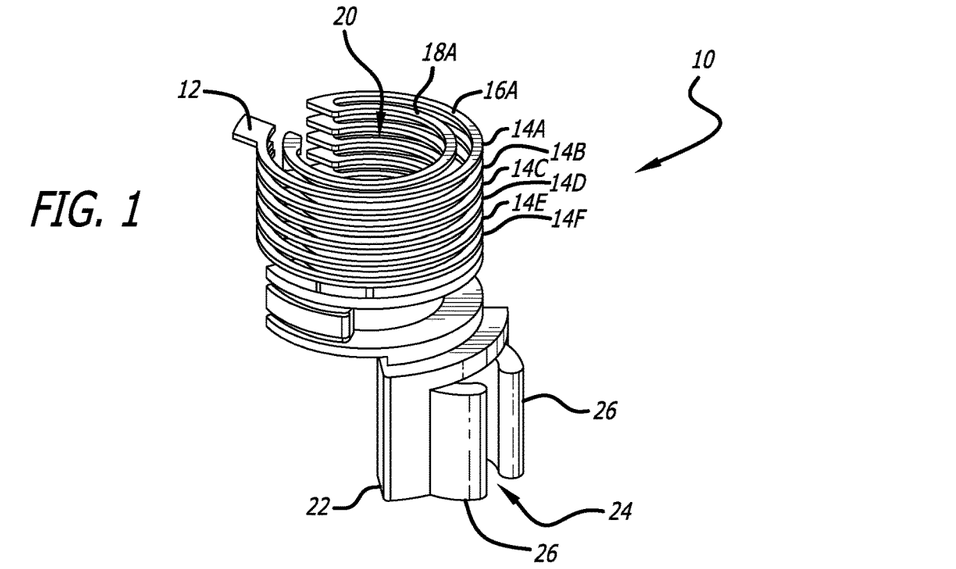
FIG. 1 is a perspective view of an embodiment of a heater element of the invention.

FIG. 1 shows an embodiment of a heater element 10 in accordance with the present invention. The heater element is a complex shape formed through an additive manufacturing process such as 3D printing.

This heater element embodiment 10 is of a unitary construction and includes a complex, double element. The double element is a continuous length of material that begins at a distal tab 12 and extends in a first plane 14A around an outer ring 16A of the C-shape, or incomplete circle shape, and then turns inwardly to form an inner ring 18A of the C-shape, in the same first plane 14A. The inner ring extends back to the other end of the C, adjacent the tab 12, at which point the element plane connects to an adjacent, second plane 14B and forms another C-shaped layer, beginning this time with the inner ring 18B and ending with an outer ring 16B. This pattern is repeated until a number of planes (six planes 14A-F are shown in the example of FIG. 1) are formed sufficient to generate enough heat to break a tether that extends through the heater and is used to connect the implant to the pusher. This repeating pattern with inner and outer rings effectively doubles the amount of element length for a given length of the heater 10. As such, the heating element 10 of the present invention can generate as much heat as a conventional heating element having twice the longitudinal length.

Through additive manufacturing, alternative complex element shapes could be developed that would not be possible with more conventional manufacturing methods. One skilled in the art will realize the present invention should not be construed to be limited to the C-shaped embodiment of FIG. 1. This is just an example of a double-layer, nested element design that generates significant heat over a short longitudinal length. Other examples may include, but are not limited to, planar wave designs, vertical wave designs, triple-nested designs, angled planes, etc.

According to one embodiment, the heater element 10 defines an internal passage 20. The internal passage 20 may be sized to solely contain a tether connecting the implant to the pusher 60. According to another embodiment, the internal passage 20 may be large enough to contain the tether and other components, such as a support mandrel or electrical wires.

Figure 4:
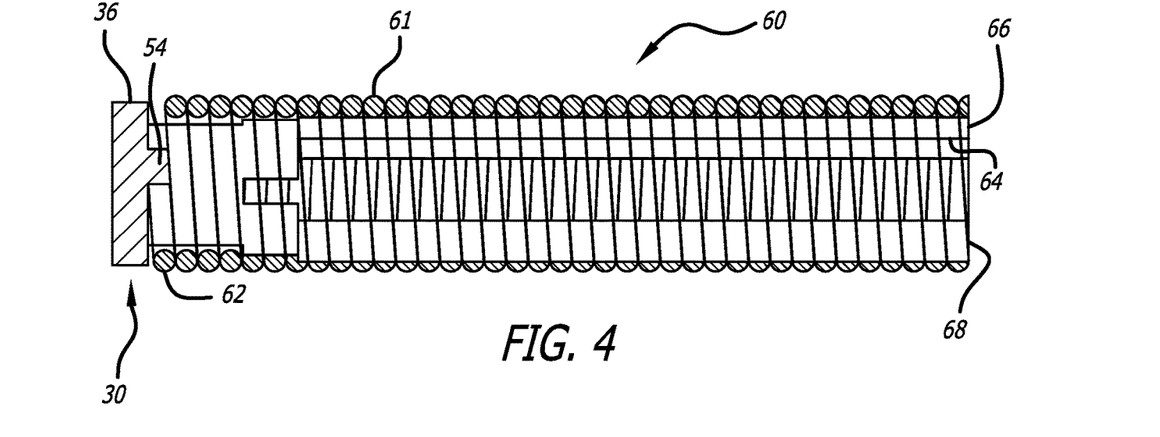
FIG. 4 is a transparent plan view of an embodiment of a pusher of the invention.

A proximal end 22 of the heater element 10 includes a passage 24 defined between tabs 26. The passage 24 is sized to receive a lead wire 68 (FIG. 4). In the example provided, the lead wire 68 is a positive lead wire. The tabs 26 are for use in joining methods such as laser welding, soldering, or the like. In one non-limiting example, the passage 24 between the tabs 26 is sized such that the terminal lead wire 68 has a friction fit between the tabs 26. Thus, the tabs 26 may hold the terminal lead wire 68 in place during a laser welding operation or other joining method. Alternatively, the tabs may be spaced apart wider than the lead wire to allow ease of insertion.

Figure 2:
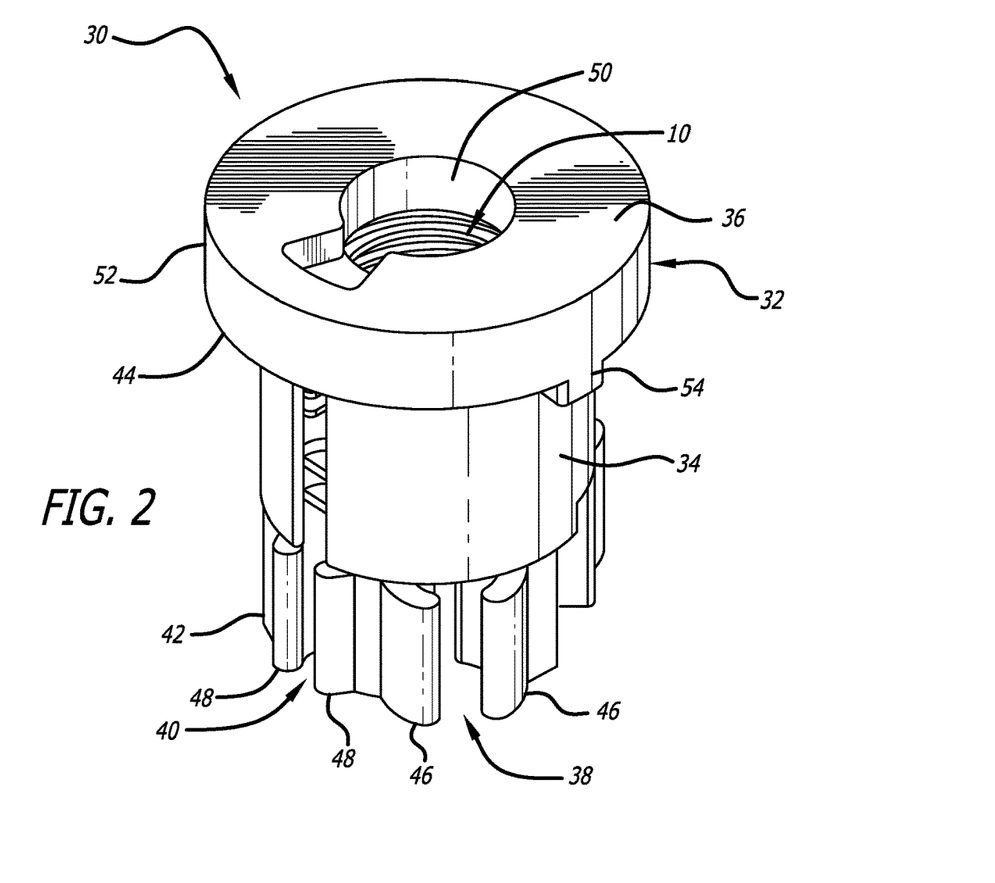
FIG. 2 is a perspective view of an embodiment of a heater capsule of the invention.
Figure 3:
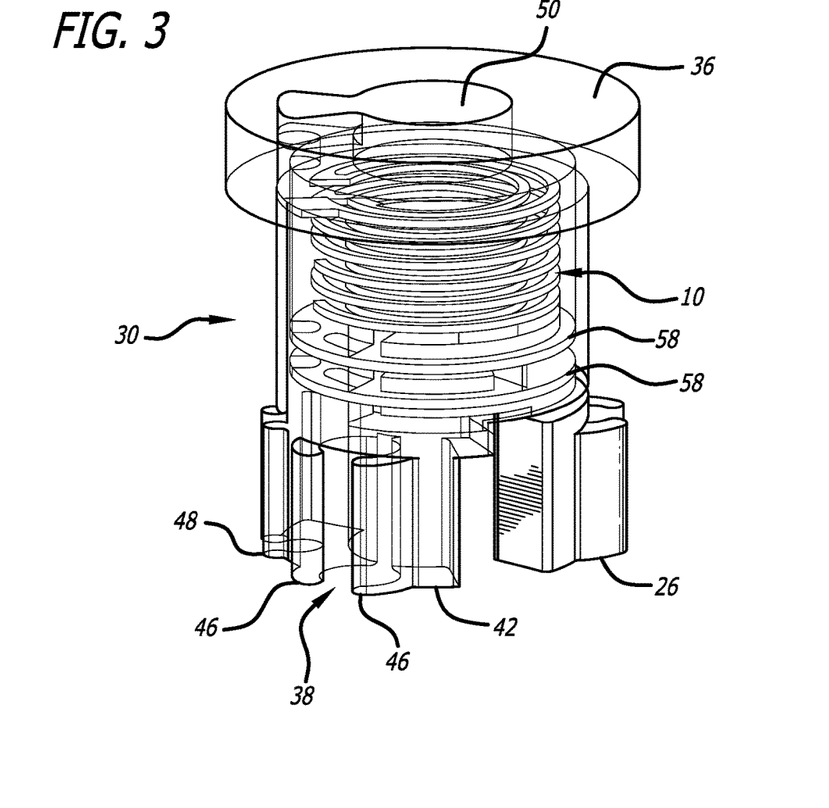
FIG. 3 is a transparent perspective view of an embodiment of a heater capsule of the invention.

FIGS. 2 and 3 show an embodiment of a heater element 10 as part of a heater capsule 30 of the invention. The heater capsule 30 may be used with a pusher 60 (FIG. 4) usable to deliver an embolic coil to a treatment site, such as an aneurysm. The heater capsule 30 generally includes an outer capsule 32 at least partially surrounding an inner heater element 10. The outer capsule 32 functions to protect the inner heater element 10 and is configured to mate with the distal end 62 of the pusher 60, as shown in FIG. 4. Once installed in the pusher, the heater capsule can be used to release an implant from a pusher, as shown FIG. 20 of U.S. Pat. No. 9,867,622 to Bowman.

In the embodiment of FIG. 2, the outer capsule 32 includes a body 34 and a cap 36. The body 34 has openings 38 and 40 at a proximal end 42 of the body 34, opposite the cap 36, which is at a distal end 44 of the body 34. The openings 38 and 40 are sized to receive wires, such as terminal leads, and include protruding tabs 46 and 48 for use in joining the leads to the tabs through the use of methods such as laser welding, soldering, or the like.

In one embodiment, opening 38 is used to receive a negative terminal lead wire 66 (FIG. 4) used in completing a circuit that provides power to the heater capsule 30. Thus, the outer capsule 32 is constructed of an electrically conductive material such as copper, silver, steel, brass, gold, and alloys thereof, just to name some non-limiting examples. Non-metallic electrically conductive materials may also be used. The opening 38 is defined by the gap between the tabs 46 and is sized to receive the terminal lead wire 66. In one example, the gap between the tabs 46 is sized such that the terminal lead wire 66 has a friction fit between the tabs 46. Thus, the tabs 46 may hold the terminal lead wire 66 in place during the laser welding operation or other joining method.

Opening 40 may be used to attach a stretch-resistant wire 64 (FIG. 2) that extends proximally through the pusher 60. The stretch resistant wire 64 may prevent a coil 61 of the pusher 60 from unduly stretching during movement within a patient. In one example, this stretch-resistant wire 64 is a stainless steel wire which can be welded to the tabs 48 using laser-welding. The stretch resistant wire 64 may also be a polymer tether. The opening 40 is defined by a gap between the tabs 48 and is sized to receive the stretch-resistant wire 64. In one example, the gap between the tabs 48 is sized such that the stretch-resistant wire 64 has a friction fit between the tabs 48 such that the tabs 48 may hold the stretch-resistant wire 64 in place during the laser welding operation or other joining method. Alternatively, the tabs may be spaced apart wider than the lead wire to allow ease of insertion.

The cap 36 of the capsule 32 defines a lumen 50, through which a tether is routed for connecting the implant to the pusher 60. The lumen 50 may have a diameter that matches or approximates the diameter of the internal passage 20 of the heater element 10. The tether passes through the heater 10 and is severed, melted or broken by the heater 10 when the heater 10 is activated in order to release the implant. The cap has a diameter that is greater than the capsule body 34 such that an overhang 52 is created. The overhang 52 acts as a stop against the pusher 60 when the capsule 32 is inserted into the distal end 62 of the pusher coil 61. A protrusion 54 extends proximally from the proximal side of the cap 36 and acts against a distal terminus 62 of the pusher coil 61.

In the example of FIGS. 1-4, the circuit providing power to the heater element 10 begins at a power source in the handle (not shown) at a proximal end of the pusher 60. The positive lead wire 68 extends through the pusher 60 and is electrically connected to the tabs 26 of the heater 10. The current flows through the inner and outer elements 18 and 16, respectively of the various planes 14F-A and up to the distal tab 12, which is electrically connected to the outer capsule 32 of the heater capsule 30. The current then flows through the outer capsule 32 to the tabs 46 and back through the negative lead wire 66 back to the power source. The current could also flow in the reverse direction, as one skilled in the art will understand.

FIG. 3 shows a transparent view of an assembled heater capsule 30. Included in this view are insulative layers 58, which ensure that the current flowing through the heater does not short to the outer capsule 32 prematurely before reaching the distal tab 12. One advantage of the 3d printing techniques used in making the heater is that the insulative layers 58 can be formed concurrently with the heater elements. The insulative layers 58 may be formed of an insulative material such as such as polyimide, parylene, and ceramic, just to name a few non-limiting examples.

Many delivery pushers used to deliver an embolic coil utilize a marker band just proximal of the embolic coil. The embodiments of FIGS. 5-7 utilize a marker band 80 that includes a proximal portion 82 that is shaped to allow more implant flexibility especially once the implant is outside of the delivery catheter. A distal portion 84 of the marker is smaller and sits within the implant while the proximal portion 82 of the marker is enlarged and has a tapered shape. The distal portion 84 of the marker supports the implant 86 while the implant 86 is connected to the delivery pusher, while the angled marker still allows a bit of freedom of movement as the implant is pushed out from the delivery catheter, thereby reducing the friction and "kick" associated with overly stiff implants during delivery. FIG. 6 is transparent to better show this distal portion 84 within the implant 86. The distal portion 84 may be welded in place.

Figure 5:
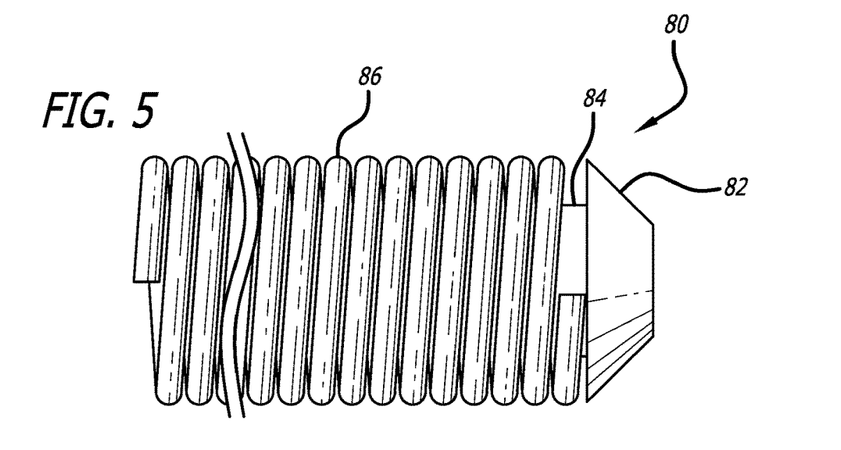
FIG. 5 is a plan view of an embodiment of a marker band of the invention inserted into a proximal end of an implantable coil.
Figure 6:
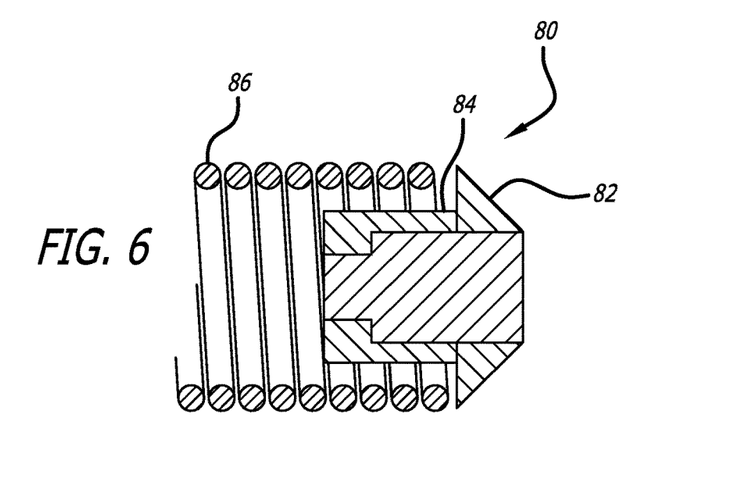
FIG. 6 is a transparent elevation of an embodiment of a marker band of the invention inserted into a proximal end of an implantable coil; and, FIG. 7 is a plan view of an embodiment of a marker band of the invention connected to a pusher.
Figure 7:
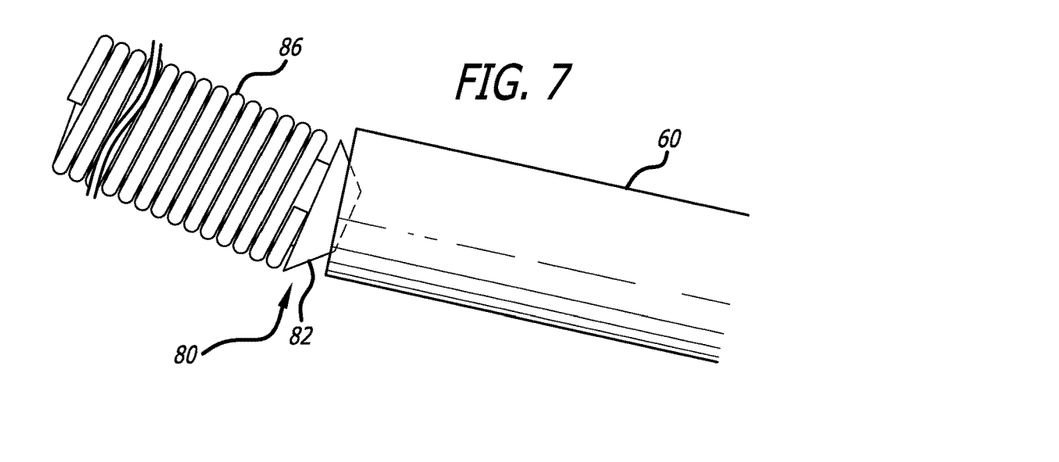

The example of FIGS. 5-7 is a straight taper, but other embodiments would also accomplish the pivot result. For example, the proximal portion 82 could be rounded, chamfered, beveled, just to name a few non-limiting examples.

FIG. 7 demonstrates how the tapered portion 82 interfaces with the cap 36 of the outer capsule 32 of the heater capsule 30. The proximal portion 82 is tapered to nest within a distal structure at the distal end of the pusher 60. Because the tapered portion 82 has a tapered diameter that is smaller than the diameter of the distal end of the pusher, the marker 80 is allowed to pivot within the distal end of the pusher, much like a ball and socket joint. This allows a greater degree of freedom when pushing the implant coil into the aneurysm.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A flexible junction between a pusher and an implantable coil comprising:
    a delivery pusher having a heater capsule at least partially contained within a distal end thereof and including:
        an outer capsule; and
        a heater element contained within said outer capsule having a C-shape and defining a plurality of planes, each plane including an inner ring and an outer ring, wherein one of said inner ring and said outer ring of each plane is connected to an inner ring or an outer ring, respectively, of an adjacent plane, said heater element further having an electrical connection to said outer capsule;
    an implantable coil having a radiopaque marker band at a proximal end thereof, said radiopaque marker band being pivotally connected to a distal structure of said delivery pusher, wherein said radiopaque marker band includes a non-spherical proximally tapered end, and wherein said non-spherical proximally tapered end of said radiopaque marker band is at least partially wedged within an exterior side of an opening of said distal structure of said delivery pusher, wherein the non-spherical proximally tapered end is comprised of a geometric shape obtained by cutting a cone or a pyramid with a plane and removing a pointed tip portion.

2. The flexible junction of claim 1 wherein said heater element is connectable to a first lead wire.

3. The flexible junction of claim 1 wherein said outer capsule is connectable to a second lead wire.

4. The flexible junction of claim 1 further comprising at least one insulative layer disposed between two of said planes.

5. The flexible junction of claim 1 wherein said heater element defines an internal passage.

6. The flexible junction of claim 5 wherein said internal passage is sized to receive a tether.

7. The flexible junction of claim 1 further comprising a stretch-resistant wire extending through said delivery pusher to said outer capsule.

8. The flexible junction of claim 7 wherein said outer capsule includes tabs used for attaching said stretch-resistant wire to said outer capsule.

9. The flexible junction of claim 1, wherein the C-shape is transverse to a longitudinal axis of said heater element.

10. The flexible junction of claim 1, wherein the geometric shape is a frustum.

11. A radiopaque marker for an implant comprising:
    a distal portion;

a non-spherical proximal portion attached to said distal portion, said non-spherical proximal portion tapering proximally such that said radiopaque marker is pivotally connected to a pusher when said radiopaque marker is at least partially inserted into a junction of said pusher, and wherein said non-spherical proximal portion is at least partially nested within an exterior side of an opening of said junction of said pusher, wherein the non-spherical proximal portion is comprised of a geometric shape obtained by cutting a cone or a pyramid with a plane and removing a pointed tip portion.

12. The radiopaque marker of claim 11 wherein said distal portion has a diameter smaller than a diameter of said non-spherical proximal portion.

13. The radiopaque marker of claim 11 wherein said distal portion is sized to fit within an implantable coil.

14. The radiopaque marker of claim 11, wherein said distal portion of said radiopaque marker sits within said implant when said radiopaque marker is pivotally connected to said pusher.

15. The radiopaque marker of claim 11, wherein said distal portion of said radiopaque marker supports said implant while said implant is connected to said pusher.

16. The radiopaque marker of claim 11, wherein said non-spherical proximal portion of said radiopaque marker is chamfered.

17. The radiopaque marker of claim 11, wherein said non-spherical proximal portion of said radiopaque marker is beveled.

18. The radiopaque marker of claim 11, wherein said non-spherical proximal portion of said radiopaque marker nests within a distal structure at a distal end of said pusher when said radiopaque marker is pivotally connected to said pusher.

19. The radiopaque marker of claim 11, wherein said non-spherical proximal portion forms a ball and socket joint with said pusher when said radiopaque marker is pivotally connected to said pusher.

20. A connection between a pusher and an implantable coil comprising:

a heater capsule means for applying heat to least partially detach the implantable coil from the pusher, the heater capsule means being at least partially contained within a distal end of the pusher;

a radiopaque connection means for pivotally connecting the pusher to the implantable coil in an attached configuration prior to detachment, the radiopaque connection means including a non-spherical proximal end that is at least partially frictionally engaged within an exterior side of an opening of said pusher, wherein the non-spherical proximal end is comprised of a geometric shape obtained by cutting a cone or a pyramid with a plane and removing a pointed tip portion.

21. A flexible junction between a pusher and an implantable coil comprising:

a delivery pusher having a heater capsule at least partially contained within a distal end thereof and including:

an outer capsule; and a heater element contained within said outer capsule having a C-shape and defining a plurality of planes, each plane including an inner ring and an outer ring, wherein one of said inner ring and said outer ring of each plane is connected to an inner ring or an outer ring, respectively, of an adjacent plane, said heater element further having an electrical connection to said outer capsule;

an implantable coil having a marker band at a proximal end thereof, said marker band being pivotally connected to a distal structure of said delivery pusher, and wherein said marker band includes a proximally tapered end, wherein the C-shape is transverse to a longitudinal axis of said heater element.

* * * * *